(12) United States Patent
Vance

(10) Patent No.: US 7,855,061 B2
(45) Date of Patent: Dec. 21, 2010

(54) FUEL FARM PROCESS FOR PRODUCING BUTANOL

(76) Inventor: Adrian George Vance, 1400 Ricca Ct., Lakeport, CA (US) 95453

( * ) Notice: Subject to any disclaimer, the term of this patent is extended or adjusted under 35 U.S.C. 154(b) by 258 days.

(21) Appl. No.: 12/214,316

(22) Filed: Jun. 19, 2008

(65) Prior Publication Data

US 2009/0317901 A1 Dec. 24, 2009

(51) Int. Cl.
*C12P 7/16* (2006.01)
(52) U.S. Cl. .................. 435/160; 435/289.1; 435/292.1
(58) Field of Classification Search .............. 435/289.1, 435/292.1, 160
See application file for complete search history.

(56) References Cited

U.S. PATENT DOCUMENTS 4,260,836 A * 4/1981 Levy ........................... 568/918
5,753,474 A * 5/1998 Ramey ........................ 435/136

OTHER PUBLICATIONS

Nakas et al., "System Development for Linked-Fermentation Production of Solvents from Algal Biomass", Nov. 1983, Applied and Envoronmental Microbiology, vol. 46 No. 5, pp. 1017-1023.*
Guerrero et al., "Study of the thermal behavior of traditional wine cellars: the case of the area of "Tierras Sorianas del Cid" (Spain)", 2005, Renewable Energy, 30, pp. 43-55.*
Patrick Ward, "Fossil Freedom—Home Page" http://www.fossilfreedom.com/index.html, Jul. 13, 2007, As captured by the Wayback Machine(http://web.archive.org/web/20070713193354/http://www.fossilfreedom.com/index.html).*
Ezeji et al.,"Bioproduction of butanol from biomass: from genes to bioreactors" Apr. 25, 2007, Current Opinion in Biotechnology, 18, pp. 220-227.*
Ramey et al., "Production of Butyric Acid and Butanol from Biomass", 2004, U.S. Department of Energy, pp. 1-103.*
Rapier, "The Problem with Biobutanol", Jun. 12, 2007, http://www.consumerenergyreport.com/2007/06/12/the-problem-with-biobutanol/, pp. 1-9.*
Rapier, "Biobutanol", May 1, 2006, http://robertrapier.wordpress.com/2006/05/01/bio-butanol/, pp. 1-3.*

* cited by examiner

Primary Examiner—Michael A Marcheschi
Assistant Examiner—Jonathan M Hurst

(57) ABSTRACT

A process for producing butanol comprising the following three phases: (1) growing algae, (2) fermenting algae and (3) separating butanol.

1 Claim, 6 Drawing Sheets n-butanol n-butanol

2-butanol 2-butanol tertiary-butanol tertiary butanol

FUEL FARM PROCESS FOR PRODUCING BUTANOL

BACKGROUND OF THE INVENTION (1) Prior Art

U.S. Pat. No. 7,374,588 discloses the preparation of an additive for Diesel fuel with the objective of reducing or eliminating oxides of nitrogen in the exhaust.

U.S. Pat. No. 6,299,774 discloses the anaerobic digestion of farm waste including corn stover and cow manure for the production of methane to be used as fuel.

U.S. Pat. No. 4,368,056 discloses the production of Diesel fuel from cheese whey and carbohydrate wastes using *Clostridium* bacteria.

U.S. Pat. No. 4,341,038 discloses growing salt water algae for their oils. Oil is squeezed out of dried or semi-dried plant mass. There is mention of a possible use as fuel, but no engineering is provided.

U.S. Pat. No. 4,073,626 discloses the preparation of fuel additives made from iron salts and aromatic "nitric acid," likely nitrates of benzene and toluene as well as nitrated aliphatic compounds for reducing slimes appearing in the tanks when Diesel fuel is stored.

(2) Field of the Invention

The equipment is simple. The product needs no refining. It is totally compatible with existing fuel use and distribution infrastructure, much of which will not be needed because the product can be made in small, local facilities that are not objectionable, unsightly, odorous, dangerous or cost more than small entity, local capitalization can abide.

Two components we need are commonly in air and soil. Single celled algae spores abound in air and bacteria are ubiquitous in soil. We can easily capture algae spores for the small, round one-cell plants and tiny rod bacteria that look like snare drum sticks with two bulbous ends.

The algae are in the genus *Chlorella, Protococus* and *Pleurococus*. They have different appearances, but all are single-celled and double in mass every day when they receive full sunlight and sufficient CO2. They consume enormous amounts of $CO_2$ and the process can be operated as a carbon sink or sequestration system earning money for putting captured carbon away if such laws are passed.

The process requires three phases: (1) growing algae, (2) fermenting algae and (3) separating butanol.

The first phase is accomplished in a clear sealed tank or clear covered tray with its atmosphere enriched with $CO_2$. Each tank will need 1500 pounds of $CO_2$, ¾ ton. The US Dept. of Energy estimates that $CO_2$ sequestration will cost $100 per ton so each tank could earn $75 per day on this basis alone.

The second phase is fermentation with *Clostridium tyrobutyricum* and *Clostridium acetobutylicum* bacteria. *Clostridium acetobutylicum* was used in 1916, during World War I, when Chime Wizemann, a disciple of Louis Pasture, discovered it would produce butanol and acetone from a wide variety of materials. In a typical fermentation, butyric, propionic, lactic and acetic acids were produced by *Clostridium acetobutylicum*. During the process the culture pH drops; the bacteria change operations to produce butanol, acetone, isopropanol and ethanol in a mix which while combustible is not ideal.

A better process has been developed using continuous immobilized cultures of *Clostridium tyrobutyricum* and *Clostridium acetobutylicum* to produce optimal butanol with a yield of up to 42 percent. In simple terms, one microbe maximizes the production of hydrogen and butyric acid, while the other converts butyric acid to butanol. Culture selection can be done to optimize the process.

Within a few days the bacilli will convert algae to 35% to 42% butanol in hours. Butanol is a water immiscible four-carbon alcohol that burns like gasoline with 100 octane performance, but has $\frac{1}{14}$th the volatility of gasoline making it much safer in use and accidents. This is a thoroughly civilized fuel that should have been in use since it was discovered in 1916, but petroleum was cheaper.

The fermentation is complete when the "must," as such mixtures are called, stop producing gases, $CO_2$ and hydrogen, which can also be collected and pumped to the growing tanks. It may be possible to select bacteria to make enough hydrogen to use the gas to heat the must and then collect a richer in $CO_2$ burner exhaust for algae tanks.

The "diversity effect," discovered by ecologists who have data showing increased growth when different species are in close proximity. The differences reported on the order of tens of percent and can be easily employed in this concept by leaving a can of carbonated water open to the air and allowing algae spores to fall into it. Then, culture the entire mix of captured spores rather than select a single species.

The key to manipulating organisms is selecting between generations. Where this takes a long time in animals and plants, it happens very fast with single celled plants and bacteria. There is a new generation every day for algae and every few hours for bacteria. If ten cultures are running and one is selected giving more desired product, it may be used to seed the next generation there improving the strain quickly. Bacteria are masters of molecular manipulation, throwing off all kinds of byproducts.

There are many kinds of single-cell algae. Some grow in fresh water; others thrive in brackish water and even more in seawater. Our atmosphere is a very poor source of carbon dioxide so $CO_2$ must be added to the culture to optimize algae growth.

As the algae culture thickens the underside becomes dark. This can be used as a signal to harvest the top half of the culture. When culture is six inches thick, the top three inches is skimmed off, piped it into a fermenting tank and cultures of *Clostridium tyrobutyricum* and *Clostridium acetobutylicum* are added for the fermentation step.

We can control-the rate of culture growth with carbon dioxide. The remaining mass should double every day. When the top half of the algae mass is removed to the fermentation tanks bacteria ferment the mass in a few days and up to 42% of it will be converted to butanol isomers.

In a prototype four by 20 foot growing cell the skimmed portion of the growing culture would be 156 gallons of algae. That algae weighs 9750 pounds and is 90% is water. It has 975 sounds of fermentable biomass, 42% of which is carbon from $CO_2$. This will produce about 60 gallons of butanol isomer mixture that is primarily n-butanol, small amounts of 2-butanol and tertiary butanol.

Starting a growing cell to the first day's harvest takes about six days from a ten pound culture seeding. From that point on nearly 1,000 pounds of algae may be skimmed from the cell every sunny day if we have supplemented it with 1500 pounds of carbon dioxide gas.

The skim is piped to 20 foot lengths of 18 inch plastic culvert pipe put on the ground or held in a steel rack sufficient to deal with 10,000 pound loadings. The rack may have six or eight tubes depending on the latitude as one tube is needed for every day the fermentation requires. A new load of algae will be ready for the next tube at the end of every day ideally.

The fermentation racks are warmed with sunlight or solar heated air drawn from above ground and burning the gas produced in the fermentation for heating if it contains enough hydrogen to be a combustible. Or, in the location where the fermentation above ground and in the sun, they will be heated naturally.

If it is kept above 25 Celsius degrees the fermentation should take three to five days. When the fermentation is complete gas production stops. At that point the fermentate "must" is dumped to the chilling cell below ground. Surrounding earth temperature is ten Celsius degrees and with additional mechanical chilling the must temperature is reduced to zero Celsius degrees, but not frozen. Butanols separate from the mixture and float to the top to be decanted. Filtration is the final step to assure the product is market ready.

The remaining fluid may not be reused for growing algae as butanol is poisonous to algae, but it may be possible to perform another extraction by chilling or icing the fluid after ten batches are collected. There will always be a butanol remainder in this liquid and at some point the remainder will have to be dealt with as waste.

Butanol is the four carbon alcohol that has three isomeric forms, the same number of carbons, hydrogens and one oxygen per molecule. The first is called "n-butanol" for "normal butanol" which has four carbon atoms in a straight chain; three are surrounded by bonded hydrogens on all carbon bonds while the last carbon has two hydrogens, but an "OH" hydroxyl unit on its last carbon bonding electron.

The "2-butanol" isomer has the "OH" bonded to the second carbon atom from the end and all other carbon bonds not connected to a carbon are bonded to hydrogens.

The final isomer, "tertiary butanol" has four carbons bonded in a four carbon "T" pattern with the OH group at the top of the "T" which makes a plus sign, "+", with the OH radical attached to the center carbon atom. While it is possible for the OH to be bonded to another of three carbons no differentiation has been made in the literature.

All butanols produce almost as much energy as 100 octane gasoline. The n-butanol is the most common and the bulk of the fermentation. It can be 85% of the product with 2,butanol making up the much of the remainder and tetra-butanol present in trace quantities.

Butanol is not miscible with water like ethanol. Ethanol molecules are so compatible with water a mixture of 50 ml each makes a solution with a volume of only 95 ml that can only be separated by distillation. And, even then not fully. Ethanol distillations typically carry over 5% water which causes problems in pipelines, pumps and fuel systems. We do not have this problem with butanol as it is not water miscible.

SUMMARY OF THE INVENTION

Fuel Farm is based on algae culture and bacterial fermentation. In the first step several species of single celled algae grow in fresh, brackish or salt water, cultured as a community in a tank exposed to sunlight entering the culture through a transparent side, cover or lid. The tank is sealed and carbon dioxide pumped into it to keep a higher than atmospheric pressure in the culture. This improves availability of the nutrient. In a day of full sunlight the culture mass doubles.

At the end of the day the top three inches of culture is skimmed off to one of several tanks immediately under the growing tank. These tanks are formed plastic used for culverts, but they may be metal or concrete. The plastic is preferred as it is fluted, transfers heat well and is cheap. They are held in a rack with air spaces between to facilitate heating, repair and replacement or they may be laid on the ground and exposed to sunlight or put in "window boxes" functioning as solar heaters.

In the underground version, air in the chamber is heated with solar collectors using air as the working fluid. Additional heat is obtained with open burners or heaters using butanol or captured fermentation gas when it has enough hydrogen to render the gas mixture combustible.

It will take six to eight fermentation tanks to accommodate the skim of one four by 20 foot algae growing tank as the growing takes one day, but the fermentation four to six. During the transfer the material is mixed with *Clostridium tyrobutyricum* and *Clostridium acetobutylicum* bacteria. They will process the algae to n-butanol in four to six days depending on temperature.

Carbon dioxide and hydrogen produced are collected for two uses: heating and culture feeding. As fermentation evolves the pH drops as more butanol is produced. The end of the fermentation is indicated by the decline in gas production signaling algae have been consumed.

The fermentation "must" is dumped to a separation tank under the fermentation tanks. The liquor is first cooled to earth temperature of 10° Celsius and then chilled to 0° Celsius degrees mechanically or with ice and 93% of the butanol in solution rises to the top of the cooling vessel from where it is decanted. The butanol is a finished product for automobiles and only needs oil and additives to be used as Diesel fuel.

DESCRIPTION OF PREFERRED EMBODIMENT

Figure 1:
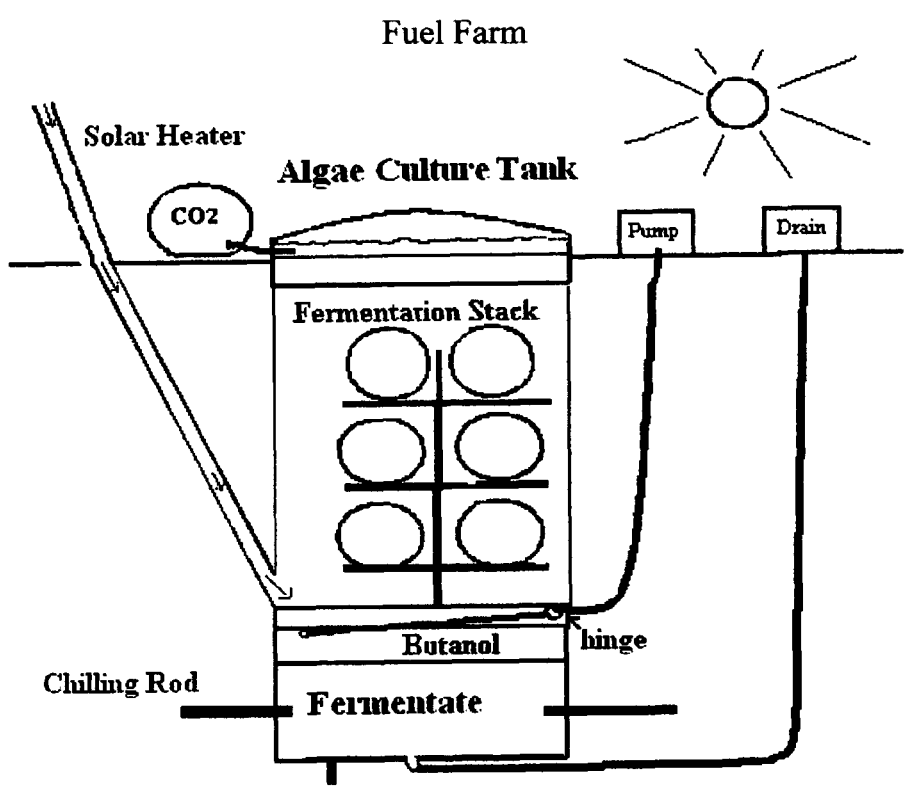
FIG. 1 shows a prototype Fuel Farm cell with the growing tank on top and six fermentation tanks below. The cooling/separation tank is seen below. Stirrers and agitators have been omitted as has gas supplemental system equipment.
Figure 2:
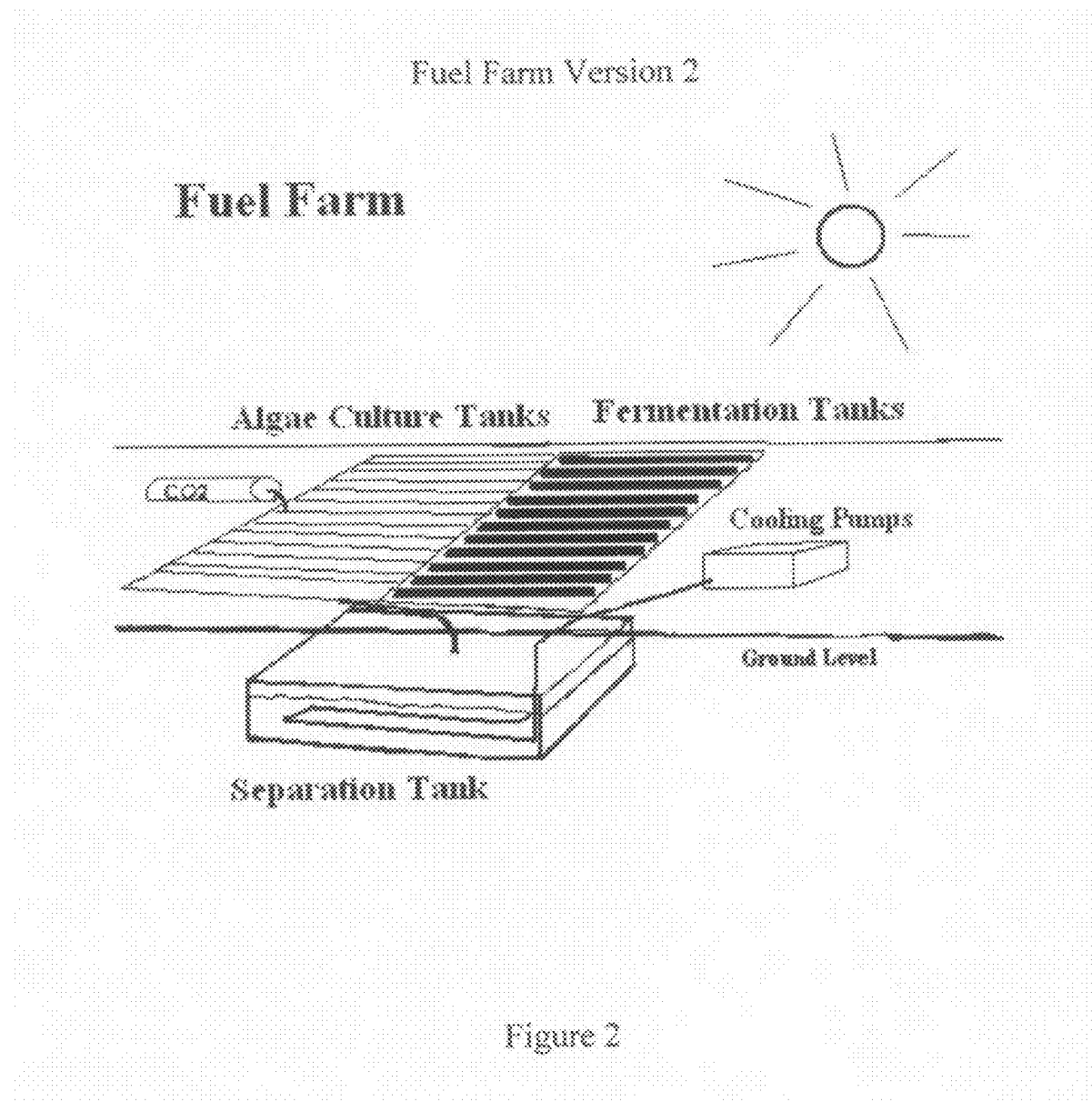
FIG. 2 shows a schematic of a fuel farm with a separation tank underground.
Figure 3:
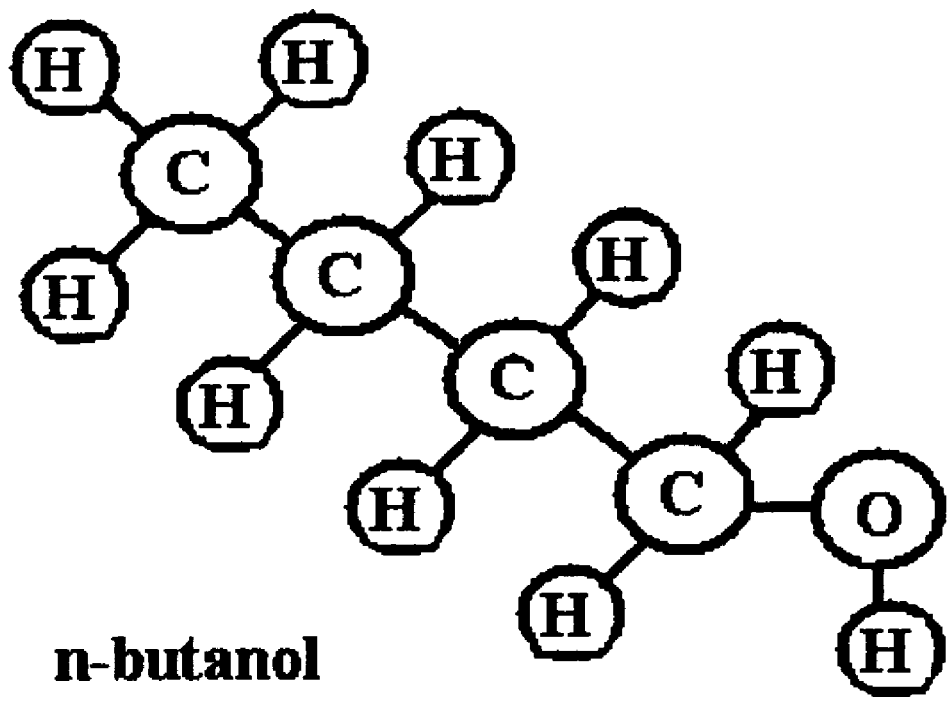
FIG. 3 shows the structure of n-butanol, the most common product of the fermentation of algae by *Clostridium tyrobutyricum* and *Clostridium acetobutylicum* bacteria
Figure 4:
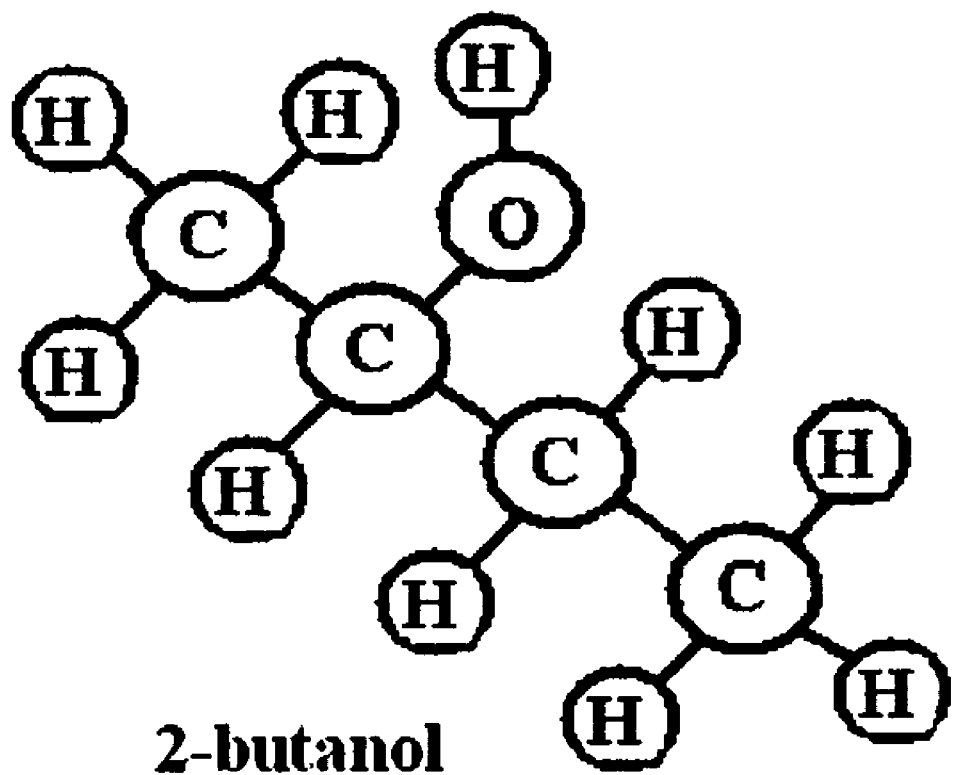
FIG. 4 shows the structure of 2-butanol, the second most common product of algae fermentation by *Clostridium tyrobutyricum* and *Clostridium acetobutylicum* bacteria
Figure 5:
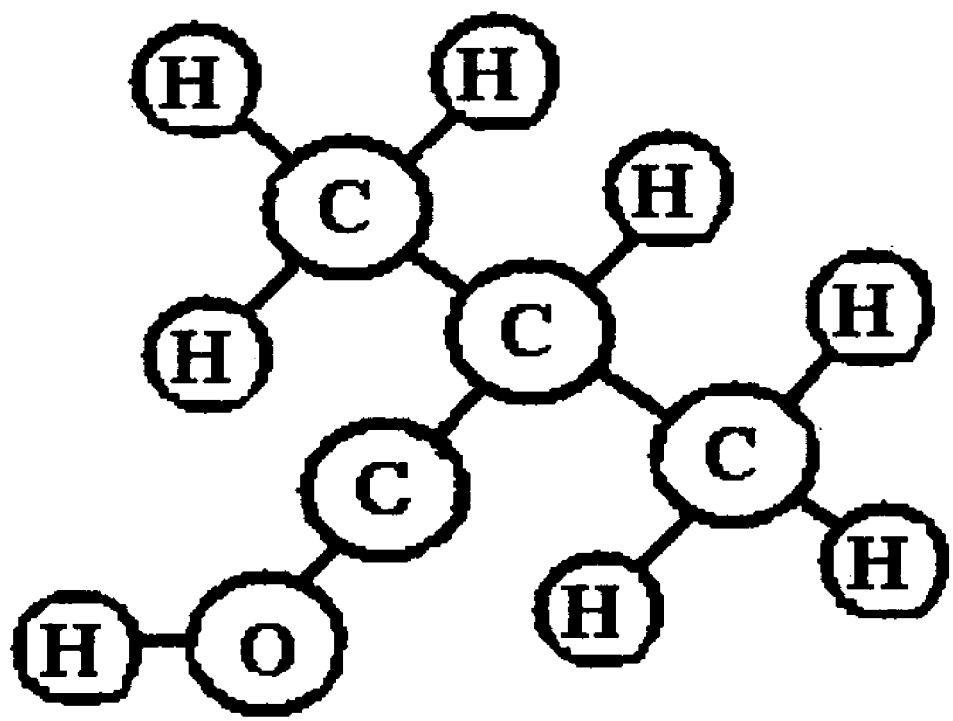
FIG. 5 shows the structure of Tertiary-butanol, the least common isomer of butanol produced by the *Clostridium tyrobutyricum* and *Clostridium acetobutylicum* fermentation.
Figure 6:
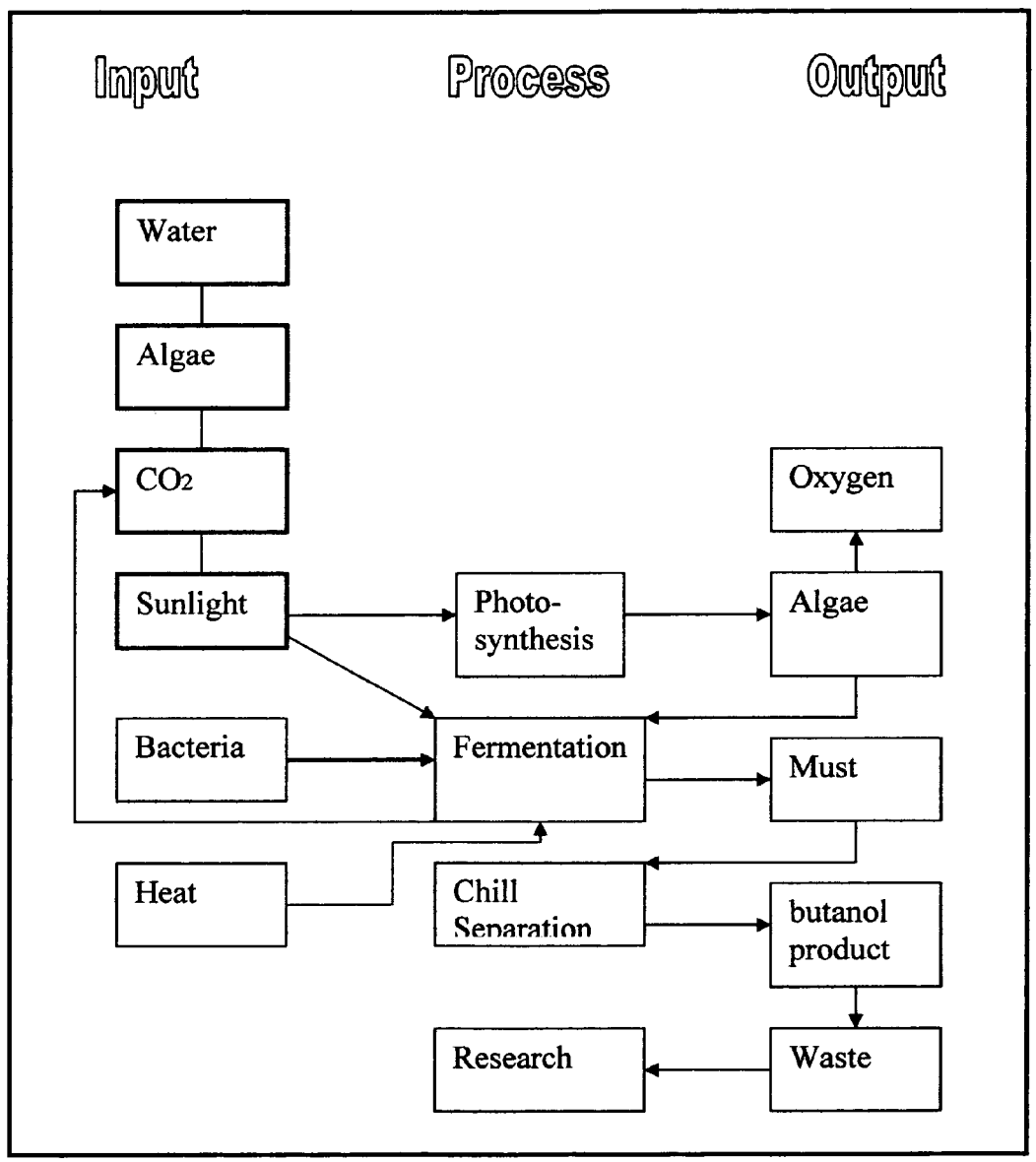
FIG. 6 depicts a Fuel Farm flow chart showing in various columns, the Input, Process and Output classifying each step of the process.

A single unit cell, scalable to any size, would include: (1) a four by 20 foot above-ground algae growing tank (2) a rack of six fermentation tanks made with 18 inch plastic culvert pipe in a rack system with six inches of space between the pipes, cantilever bracing and end caps such that the pipes may be easily replaced. (3) induction channels for hot air from the solar air heaters and provision for air heaters to burn butanol or hydrogen $CO_2$ mix if the fermentation as is combustible.

This facility will require a four foot by 24 foot trench dug into the earth and at one end we will need an additional four by four by ten foot hole for the chilling/separation tank. This tank is deeply placed to take full advantage of the earth temperature of 10° Celsius requiring cooling only to 0° Celsius to effect separation. It includes a bottom drain with an electrically or mechanically operated plug control in the tank.

Decanting is achieved with a long pipe on a flex connection such that the pipe can fall with the level of butanol as it is removed. A float with a conductivity sensor/shutoff at the end of the pipe in order that it will detect water immediately when the butanol is removed. The separation process is not 100% efficient, and butanol carried over could poison the next growing phase so the culture solution must be pumped to another tank.

Separation may be improved by waiting overnight and drawing the decantation the next day before pumping the remainder to the waste tank or dumping it. This will require keeping the tank cold overnight. This unit produces 60 gallons of butanol fuel per day or 22,000 gallons per year. This is enough for 22 large automobiles or 44 small cars for a year or 11 large autos and 11 homes in much of the United States from what could be a back yard unit running automatically and needing only two hundred gallons of water ever day plus the $CO_2$. This process literally turns water sunlight and $CO_2$ into fuel. The unit should be buildable for $10,000 to $20,000 depending on location and have a return on investment of four to eight months if the fuel were valued at $2.50 per gallon which is the estimated 1965 price equivalent inflation considered.

I claim:

1. A process for producing butanol from common algae, ubiquitous bacteria, water, sunlight and carbon dioxide consisting essentially of the following steps:
   a. collecting aerial algae spores and soil bacteria;
   b. culturing said algae in water in clear tanks exposed to sunlight by pressurizing said tanks with carbon dioxide and placing said pressurized tanks in sunlight;
   c. agitating the tanks;
   d. harvesting said cultured algae by skimming the top 3 inches of the culture;
   e. transferring the skimmed portion to a tank for fermentation, wherein the tank comprises bacteria of the genus *Clostridium* and further wherein the end of fermentation is indicated by the decline in gas production;
   f. placing the fermented culture in an underground tank to cool the contents thereof to an earth temperature of 10° C. and then subjecting the cooled culture to chilling at 0° without freezing to effect separation of butanol from the chilled culture; and
   g. decanting the butanol that has risen to the top of the tank.

* * * * *